United States Patent [19]
Sulkowski et al.

[11] 3,936,471
[45] Feb. 3, 1976

[54] (HEXAHYDROBENZIMIDAZOL-2-YL)BENZOPHENONES AND DERIVATIVES

[75] Inventors: Theodore S. Sulkowski, Wayne; Albert A. Mascitti, Norristown, both of Pa.

[73] Assignee: American Home Products Corporation, New York, N.Y.

[22] Filed: Aug. 7, 1974

[21] Appl. No.: 495,358

[52] U.S. Cl............ 260/309.6; 260/556 R; 424/273
[51] Int. Cl.²......................................... C07D 49/34
[58] Field of Search.................................. 260/309.6

[56] References Cited
UNITED STATES PATENTS
3,717,658   2/1973   Metlesics et al................. 260/309.6

FOREIGN PATENTS OR APPLICATIONS
1,187,009   4/1970   United Kingdom.............. 260/309.6
1,258,946   12/1971   United Kingdom.............. 260/309.7

OTHER PUBLICATIONS
Arient et al., Chem. Abstracts, 66:473o3d.

*Primary Examiner*—Ethel G. Love
*Attorney, Agent, or Firm*—Stephen Venetianer

[57] ABSTRACT

(Hexahydrobenzimidazol-2-yl)benzophenones are prepared by reaction of the ψ-acid chloride of an o-aroyl benzoic acid with an N-monotosyl-1,2-diaminocyclohexane, and heating the resulting benzoyl benzamide product with sulfuric acid. The intermediate benzoyl benzamides are also claimed as are the benzophenones. The compounds are useful in hyperglycemia therapy.

7 Claims, No Drawings

(HEXAHYDROBENZIMIDAZOL-2-YL)BENZOPHENONES AND DERIVATIVES

DESCRIPTION OF THE INVENTION (Hexahydrobenzimidazol-2-yl)benzophenones are prepared according to this invention by contacting the appropriate benzoyl benzamide with sulfuric acid. Thus (hexahydrobenzimidazol-2-yl)benzophenones of the formula

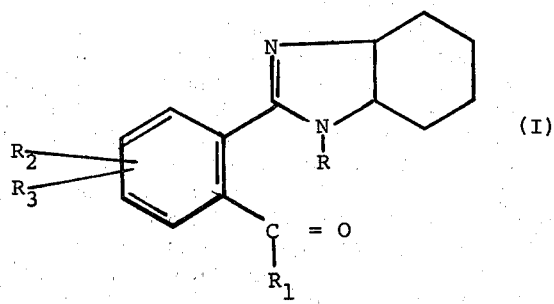

wherein R is hydrogen or (lower)alkyl; $R_1$ is selected from the group consisting of phenyl, monohalophenyl, dihalophenyl, mono(lower)alkyl-phenyl, di(lower)alkylphenyl, trifluoromethylphenyl, mono(lower)alkoxyphenyl di(lower) alkoxyphenyl, $R_2$ is selected from the group consisting of hydrogen, halogen, (lower)alkyl and (lower)alkoxy; $R_3$ is hydrogen when $R_2$ and $R_3$ are dissimilar and when $R_2$ and $R_3$ are the same they are both selected from the group consisting of hydrogen, halogen, (lower)-alkyl and (lower)alkoxy; are obtained when a benzoyl benzamide of the formula

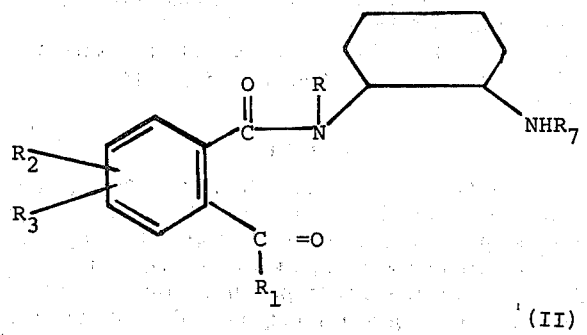

wherein R, $R_1$, $R_2$ and $R_3$ are as defined above and $R_7$ is selected from the group consisting of lower alkylsulfonyl, phenylsulfonyl, monohalophenylsulfonyl, dihalophenylsulfonyl, mono(lower) alkylphenylsulfonyl, di(-lower)alkylphenylsulfonyl and lower alkoxyphenylsulfonyl, is contacted with sulfuric acid of from about 90 to 100% concentration, preferably heated on a steam bath from 0.25 to 0.75 hour and allowed to stand at room temperature for from 4 to 24 hours, preferably 15 to 18 hours. The reaction mixture is worked up conventionally such as by quenching with water and adjusting the pH to above 7 with a base. Where R is lower alkyl, the product of formula (I) precipitates in the benzophenone form. Where R is hydrogen the product precipitates as the 5a, 6, 7, 8, 9, 9a-hexahydro-isoindolo [2, 1-a]benzimidazol-11-ol. In either case, the product in the form of the free base can then be reacted with a pharmaceutically acceptable acid to form the acid addition salt. The acid addition salt of the hexahydroisoindolo [2, 1-a]benzimidazol-ol is in the benzophenone form and becomes 2-(3a, 4, 5, 6, 7, 7a-hexahydrobenzimidazol-2-yl)benzophenone, hydrochloride, for example. For the change in forms, note U.S. Pat. No. 3,763,178, issued Oct. 2, 1973, incorporated herein by reference.

The intermediate benzoyl benzamides are prepared by reaction of the ψ-acid chloride of an appropriate o-aroyl benzoic acid of the formula

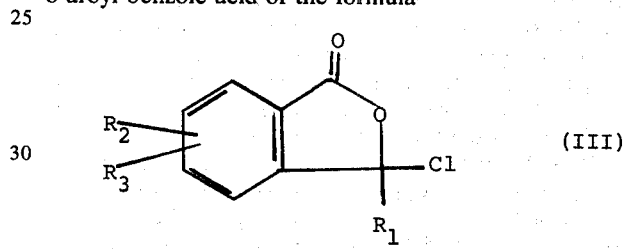

wherein $R_1$, $R_2$ and $R_3$ are as above identified with an N-monotosyl-1,2-diaminocyclohexane of the formula

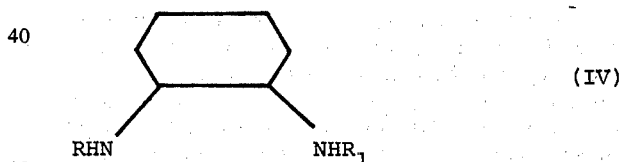

wherein R and $R_7$ are as above identified. The reaction can be carried out in pyridine or in a solvent such as dichloromethane in the presence of a base such as triethyl amine, pyridine or N,N-dimethyl aniline. Other inert solvents include toluene, benzene, chloroform, diethyl ether, acetone and the like.

The materials of formula (III) are readily prepared from the keto acids by standard procedures well known to the art.

The materials of formula (IV) are prepared directly by reaction of the appropriate diamine with the appropriate tosyl chloride.

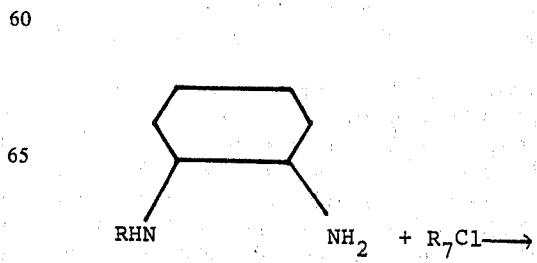

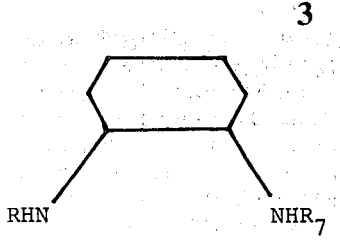

As employed herein the term (lower)alkyl includes straight and branched chain hydrocarbon moieties of from 1 to about 4 carbon atoms such as methyl, ethyl, propyl, i-propyl and butyl. The term (lower)alkoxy includes hydrocarbonoxy groups which contain from 1 to about 6 carbon atoms such as methoxy ethoxy, propoxy, butoxy and hexoxy. The term "halogen" and "halo" as used herein include bromine, fluorine, chlorine and iodine.

The compounds of this invention are useful in hyperglycemia therapy. For example, the compounds were active in the following test: Male rats weighing 170–200 grams are fasted overnight, a control blood sample is taken from the tail and a test dose of 60 mg/kg is administered by stomach tube. Subsequent blood samples are taken at hourly intervals for 5 hours. In general, a compound is considered active if a depression in blood sugar approximating 20% is observed for at least 3 of the 5 hour test period.

In addition the compounds of Example 5, 6 and 8 have anti-reserpine activity, the compounds of Examples 6 and 7 have both anti-arrhythmic and anti-ulcerogenic activity and the compound of Example 8 has anorexiant activity.

The compounds of this invention may be administered alone or in combination with pharmaceutically acceptable carriers, the proportion of which is determined by the solubility and chemical nature of the compound selected, the chosen route of administration, and standard pharmaceutical practice. For example, they may be administered orally in the form of tablets or capsules, which may contain conventional excipients, or in the form of solutions; or they may be injected parenterally, that is intramuscularly, intravenously or subcutaneously. For parenteral administration, they may be used in the form of sterile solutions containing other solutes, for example, enough saline or glucose to make the solutions isotonic.

The dosage of the present therapeutic agents will vary with the form of administration and the particular compound chosen. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects. Such a concentration level to relieve hyperglycemia will generally be within the range of about 10 to about 80 mg/kg of animal body weight.

The processes of this invention and the new and novel compounds prepared thereby are illustrated by the following examples. In examples XIII and IX, wherein R is hydrogen, the process employed is that of U.S. Pat. No. 3,423,421, issued Jan. 21, 1969, except that 1,2-diaminocyclohexane is employed instead of an o-phenylene diamine to prepare the hexahydroisoindolobenzimidazolones instead of the isoindolobenzimidazolones. The hexahydroisoindolobenzimidazolones are then tosylated and further reacted with a mineral acid as described in U.S. Pat. No. 3,763,178, issued Oct. 2, 1973.

EXAMPLE I

Part I

100 Grams of 1,2-diaminocyclohexane (mainly trans) and 200 ml of dichloromethane were stirred and cooled in an ice bath. A solution of 55 grams of p-toluene sulfonylchloride in 200 ml of dichloromethane was added dropwise while the temperature was kept below 15°C. The admixture was stirred at room temperature for 1 hour, filtered, the filtrate was extracted once with 500ml water, and the organic layer was extracted with 500 ml of a 15% hydrochloric acid. The acid extract was made basic with sodium carbonate solution, extracted with ethyl acetate and dried over magnesium sulfate. The ethyl acetate extract was evaporated to a viscous residue, triturated with ether, the solid being filtered, reslurried with ether and filtered and dried to obtain a mixture of cis and trans(mainly trans)-N-(2-aminocyclohexyl)-p-toluene-sulfonamide, 41 grams, having a melting point of 72°–75°C. Upon standing, 8 grams of a second crop was obtained from the ether having a melting point of 85°–89°C.

Part II

35 Grams of monotosyl-1,2-diaminocyclohexane from above, 200 ml dichloromethane and 30 ml of triethylamine were stirred and cooled in an ice bath. A solution of 13 grams of acetyl chloride in 75 ml of dichloromethane was added dropwise while maintaining the temperature below 15°C. The admixture was stirred at room temperature for one-half hour, extracted with 250 ml of 15% hydrochloric acid, the organic phase washed with water and dried over magnesium sulfate, filtered and evaporated to dryness. The gummy residue was triturated with ether until it solidified. The solids were separated and washed with ether to obtain 38 grams of a mixture of cis and trans(mainly trans) N-(2-acetamidocyclohexyl)-p-toluenesulfonamide. The product was recrystallized from ethylacetate with charcoal treatment to yield a product with a melting point of 157°–160°C.

Anal: Calculated for $C_{15}H_{22}N_2SO_3$: C, 58.03; H, 7.14; N, 9.03; S, 10.33. Found: C, 58.22; H, 7.94; N, 9.01; S, 10.59.

Part III

34 Grams of $N^1$-tosyl-$N^2$-acetyl-1,2-diaminocyclohexane from above were added in portions to a stirred suspension of 10 grams of $LiAlH_4$ in 750 ml of ether, stirred at room temperature for one hour after addition was completed, then refluxed for 18 hours. The reaction mixture was decomposed by dropwise addition of water, filtered and the filter cake was extracted with 800 ml of hot ethyl acetate. The organic solutions were combined and evaporated to dryness. The oily residue was dissolved in dichloromethane, dried over magnesium sulfate and evaporated to dryness. The residue was cooled, triturated with a small volume of ether and the solids separated to yield 29 grams of a mixture of cis and trans (mainly trans) N-(2-ethylaminocyclohexyl)-p-toluenesulfonamide, melting point 82°–90°C.

EXAMPLE II

A solution of 20 grams of ψ-acid chloride of o-(p-chlorobenzoyl)benzoic acid and 60 ml of methylenechloride was added slowly with stirring to a solution of 22 grams of N-(2-ETHYLAMINO-CYCLOHEXYL)-p-TOLUENE SULFONAMIDE (mainly trans), from Example I,125 ml of methylenechloride and 20 ml of triethylamine. After addition was completed, the mixture was stirred and refluxed for three hours. The mixture was extracted with water and with 10% hydrochloric acid. The methylenechloride solution was dried over magnesium sulfate then evaporated to dryness. The residue was triturated with ether and filtered to obtain a mixture of cis and trans 2-(p-CHLOROBENZOYL)-N-[2-(p-TOLUENE-SULFONAMIDO)CYCLOHEXYL]N-ETHYLBENZAMIDES.

The above solid and 300 ml of ethyl acetate were heated to reflux, then filtered to remove undissolved solids. The separated solid was recrystallized from a large volume of ethylacetate to obtain cis-2-(p-CHLOROBENZOYL)-N-[2-(p-TOLUENESULFONAMIDO)CYCLOHEXYL]-N-ETHYLBENZAMIDE, mp. 213–5°C.

Anal: Calculated for $C_{29}H_{31}N_2ClSO_4$: C,64.61; H,5.80; N,5.20; Cl,6.58; S,5.95. Found: C, 64.83; H,6.01; N,5.31; S,6.09; Cl,6.68.

The ethyl acetate filtrate from the treatment of the mixed benzamides, was evaporated to dryness. The solid residue was recrystallized from ethyl acetate to obtain trans-2-(p-CHLOROBENZOYL)-N-[2-(p-TOLUENESULFONAMIDO)CYCLOHEXYL]-N-ETHYLBENZAMIDE, mp. 178°–180°C.

Anal: Calculated for $C_{29}H_{31}N_2Cl SO_4$: C, 64.61; H,5.80; N,5.20; Cl,6.58; S,5.95. Found: C, 64.75; H,5.94; N,5.16; S,5.69; Cl,6.86.

EXAMPLE III

Eighteen grams of trans 1,2-diamino-cyclohexane sulfate was suspended in 100 ml of warm water and made basic with 50% sodium hydroxide solution. The mixture was extracted with benzene. The benzene solution was dried over magnesium sulfate and evaporated to dryness. The residual oil was dissolved in 35 ml of methylenechloride and cooled to 5°C. A solution of 4 grams of p-toluenesulfonyl chloride and 20ml of methylenedichloride was added to the above solution while maintaining the temperature between 5° and 10°C. The mixture was stirred an additional 10 minutes, then extracted with 100 ml of water. The methylenechloride solution was extracted with 75ml of 15% hydrochloric acid. The acid portion was made basic with saturated sodium carbonate solution and extracted with ethyl acetate. The ethyl acetate extract was dried over magnesium sulfate, then evaporated to dryness. The residue was triturated with a small volume of ether and filtered to obtain trans N-(2-AMINOCYCLOHEXYL)-p-TOLUENESULFONAMIDE, mp. 93-5°C.

Anal: Calculated for $C_{13}H_{20}N_2SO_2$: C, 58.18; H, 7.51; N, 10.43; S, 11.95. Found: C, 58.32; H, 7.52; N, 10.34; S, 11.70.

Three grams of the above material was dissolved in 50 ml of methylene chloride. Five ml of triethylamine was added and the solution was cooled in an ice bath. A solution of 1.2 grams of acetyl chloride in 10 ml of methylenechloride was added in small portions with stirring. The mixture was left at room temperature for 1 hour. The mixture was extracted successively with 10% hydrochloric acid, water, and saturated sodium carbonate solution. The methylene chloride solution was dried over magnesium sulfate, then evaporated to dryness. THe residue was recrystallized from ethyl acetate to obtain trans N-(2-ACETAMIDOCYCLOHEXYL)-p-TOLUENESULFONAMIDE, mp. 174–6°C (resolidifies and remelts at 182-4°C).

Anal: Calculated for $C_{15}H_{22}N_2SO_3$: C, 58.03; H, 7.14; N, 9.03; S, 10.33. Found: C, 57.91; H, 7.17; N, 901; S, 10.23.

Twenty-three grams of trans-N-(2-ACETAMIDOCYCLOHEXYL)-p-TOLUENESULFONAMIDE was added in portions to a stirred suspension of 7 grams of lithium aluminium hydride and 500ml of anhydrous ether. The mixture was stirred and refluxed for 17 hours. The mixture was decomposed by dropwise addition of water and filtered. The filter cake was extracted with a total of 750 ml of boiling ethyl acetate. The organic portions were combined, dried over magnesium sulfate, then evaporated to dryness. The residue was slurried with ether and filtered. On recrystallization from ether there was obtained trans N-(2-ETHYLAMINOCYCLOHEXYL)-p-TOLUENESULFONAMIDE, mp. 112–4°C.

Anal: Calculated for $C_{15}H_{24}N_2SO_2$: C, 60.77; H,8.16; N, 9.95; S, 10.82. Found: C, 61.01; H, 8.23; N, 9.32; S, 10.86.

EXAMPLE IV 8.5 Grams of the ψ-acid chloride of o-(p-chlorobenzoyl) benzoic acid, 9 grams of trans N-(2-ethylaminocyclohexyl)-p-tolnenesulfonamide from Example III, 100 ml dichloromethane and 25ml of triethylamine were refluxed for 2 hours. The reaction mixture was extracted with water, the organic phase was then extracted with 75 ml of 10% hydrochloric acid, washed with sodium carbonate solution, dried over magnesium sulfate, and evaporated to dryness. The residue was triturated with ether and the solid was separated and washed with ether to obtain 7 grams of material which was recrystallized form ethyl acetate. The first crop of 3.3 grams melted at 180°–182°C. and was pure trans 2-(p-chlorobenzoyl)-N-[2-(p-toluenesulfonamido)cyclohexyl]-N-ethyl benzamide.

Anal: Calculated for $C_{29}H_{31}N_2ClSO4$: C, 64.75; H, 5.94; N, 5.16; Cl 6.86; S, 5.69. Found: C, 64.76; H, 5.83; N, 5.08;Cl, 6.41; S, 5.84.

EXAMPLE V

17 Grams of the trans isomer of 2-(p-chlorobenzoyl)-N-[2-(p-toluenesulfonamido)cyclohexyl]-N-ethylbenzamide from Example II and 50 ml of 96% sulfuric acid were heated in a steam bath for 35 minutes then left at room temperature for 18 hours. The admixture was quenched with ice water, extracted with ethyl acetate and back extracted with water. The aqueous portions were combined, made basic with 50% sodium hydroxide solution and extracted with ethyl acetate. The ethyl acetate portion was washed with water, dried over magnesium sulfate and evaporated to dryness to obtain 6.5 grams of residual oil. The oil was dissolved in 30 ml of ether, the solid crystallixed on standing and was filtered and washed with ether (very soluble in ether) to yield 1.5 grams melting at 105°–107°C. The ether filtrate was saturated with hydrogen chloride, left standing overnight, separated by filtration and the solid was washed with a 1:1 mixture of ether and acetone and dried in vacuo to yield 4.5 grams melting at 181°–185°C with decomposition.

The solid was recrystallized from a mixture of ethanol and ethyl acetate to yield 2 grams, melting at 198.5°–201°C, of the trans isomer of 4'-chloro-2-(1-ethyl-3a, 4, 5, 6, 7, 7a-hexahydrobenzimidazol-2-yl)benzophenone hydrochloride. Analysis calculated for $C_{22}H_{23}N_2ClO.HCl$ C,65.51; H,6.00; N,6.94; Cl,17.58. Found: C,65.37; H,5.98; N,7.11; Cl,17.28.

EXAMPLE VI

A mixture of 7.5 grams of cis-2-(p-CHLOROBENZOYL)-N-[2-(p-TOLUENESULFONAMIDO)CYCLOHEXYL]-N-ETHYLBENZAMIDE from Example II and 25ml of 96% sulfuric acid was heated in a steam bath for 35 minutes, then left standing at room temperature for 15 hours. The mixture was quenched with 250ml of ice water and extracted with ethyl acetate. The aqueous portion was cooled and made basic with 50% sodium hydroxide solution. The mixture was extracted with ethyl acetate. The ethyl acetate portion was extracted with water, dried over magnesium sulfate, then evaporated to dryness. Residual oil solidified on standing. The solid, mp. 73–6°C, was dissolved in ether and saturated with hydrogen chloride. The solid was separated by filtration. On recrystallization from ethanol-acetone there was obtained cis 4'-CHLORO-2-(1-ETHYL-3a, 4, 5, 6, 7, 7a-HEXAHYDROBENZIMIDAZOL-2-YL) BENZOPHENONE HYDROCHLORIDE, mp. 219°–221°C.

Anal: Calculated for $C_{22}H_{23}N_2ClO.HCl$; C, 65.51; H,6.00; N,6.94; Cl,17.58. Found: C,65.35; H,6.18; N,7.09; Cl,17.96.

EXAMPLE VII

Twenty-four grams of trans N-(2-ETHYLAMINOCYCLOHEXYL)-p-TOLUENESULFONAMIDE from Example III, 200 ml of methylenechloride, 24ml of triethylamine and 20 grams of ψ-acid chloride of o-benzoylbenzoic acid were mixed together and refluxed 4 hours. The mixture was extracted successively with water, 15% hydrochloric acid, and saturated sodium carbonate solution. The methylenechloride solution was dried over magnesium sulfate, then evaporated to dryness. The residue was slurried with ethyl acetate and filtered. Recrystallization from ethyl acetate afforded trans-2-BENZOYL-N-[2-(p-TOLUENESULFONAMIDO)CYCLOHEXYL]-N-ETHYL BENZAMIDE, mp. 201.5°–204°C.

Anal: Calculated for $C_{29}H_{32}N_2SO_4$: C, 69.02; H,6.39; N,5.55; S,6.35. Found C, 69.00; H,6.52; N,5.16; S,6.58.

Thirty-five grams of trans-2-BENZOYL-N-[2-(p-TOLUENESULFONAMIDO)CYCLOHEXYL]-N-ETHYLBENZAMIDE and 75ml of 96% sulfuric acid were mixed and heated in a steam bath for 40 minutes, then left at room temperature for 16 hours. The mixture was quenched with 700ml of ice water and the whole extracted with ethyl acetate. The aqueous portion was cooled and made basic with 50% sodium hydroxide solution. The mixture was extracted with ethyl acetate. The ethyl acetate portion was extracted with water, dried over magnesium sulfate, then evaporated to dryness. The oily residue was dissolved in 25ml of ether-75ml of hexane. Solid precipitated on standing. On recrystallization from diethyl ether-hexane there was obtained trans 2-(1-ETHYL-3a, 4, 5, 6, 7, 7a-HEXAHYDRO-BENZIMIDAZOL-2yl) BENZOPHENONE, mp. 80–3°C.

Anal: Calculated for $C_{22}H_{24}N_2O$; C,79.48; H,7.28; N,8.43. Found C,79.33; H,7.49; N,8.33.

EXAMPLE VIII

A mixture of 75 grams of o-(p-chlorobenzoyl)benzoic acid, 75ml of 1,2-di-aminocyclohexane (mainly trans), and 150ml of toluene was refluxed 19 hours in a flask equipped with a water separator. The solution was extracted with water, then filtered to remove the insoluble material. The toluene portion was evaporated to dryness. The residue was slurried with ethanol and filtered to afford 4-b-(p-CHLOROPHENYL)-4b, 5, 6, 7, 8, 9,-HEXAHYDROISOINDOLO[2,1-a]-11 H-BENZIMIDAZOL-11-ONE (mainly trans), mp 172–5°C. The latter compound is described in an article by Aeberli and Houlihan in The Journal of Organic Chemistry, Vol.34, No. 6, June 1969, (pages 1720–1726), particularly compound 13e.

The above material, 32 grams of p-toluenesulfonyl chloride and 100ml of pyridine were refluxed 24 hours. The mixture was evaporated to dryness. The residue was triturated with ethyl acetate and the solid was separated by filtration. Recrystallization from ethanol afforded trans-4b(p-CHLOROPHENYL-5-(p-TOLYLSULFONYL)-4b, 5, 6, 7, 8, 9-HEXAHYDROISOINDOLO[2,1-a]-11 H-BENZIMIDAZOL-11-ONE, mp. 207°–210°C.

Anal: Calculated for $C_{27}H_{25}N_2ClSO_3$: C, 65.77; H,5.11; N,5.68. Found C, 65.65 H,5.32; N,5.65.

Forty grams of the above material and 80ml of 90% sulfuric acid were heated in a steam bath until solution occurred, then left standing at room temperature for 3.5 hours. The mixture was quenched with 750ml of ice water. The mixture was filtered to remove precipitated material. The separated solid was shaken with ethyl acetate and saturated sodium carbonate solution. The ethyl acetate portion was evaporated to dryness. The solid was slurried with 95% ethanol and separated; mp. 188°–191°C.

Aqueous mother liquors (from initial quench) were made basic with 50% sodium hydroxide solution. The precipitated solid was separated and dried; mp. 185–9°C. This material was combined with above solid and dissolved in ethanol. The solution was saturated with hydrogen chloride and evaporated to dryness. The residue was recrystallized from ethanol-acetone to obtain trans 4-CHLORO-2-(3a, 4, 5, 6, 7, 7a-HEXAHYDROBENZIMIDAZOL-2-YL)BENZOPHENONE, HYDROCHLORIDE, mp. 210°–212°C (dec.). (Resolidifies on heating, remelts at 274°–277.5°C).

Anal: Calculated for $C_{20}H_{19}ClN_2O.HCl$: C, 64.00; H,5.37; N,7.46; Cl,18.91. Found C, 64.29; H,5.33; N,7.40; Cl,18.97.

EXAMPLE IX

A mixture of 125 grams of o-benzoyl-benzoic acid, 300ml of toluene and 200 grams of 1,2-diaminocyclohexane (mainly trans) was refluxed 19 hours in a flask equipped with a water separator. The solution was cooled, extracted with water and with saturated sodium carbonate solution. The toluene portion was evaporated to dryness. The residue was slurried with ethanol and filtered. The solid was recrystallized from ethanol to afford 4b, 5, 6, 7, 8, 9-HEXAHYDRO-4-b-PHENYL ISOINDOLO[2,1-a] 11 H-BENZIMIDAZOL-11-ONE, mp. 143–5°C.

Anal: Calculated for $C_{20}H_{20}N_2O$: C,78.91; H,6.62; N,9.21. Found C,78.92; H,6.62; N,9.24.

A mixture of 90 grams of the above material, 63 grams of p-toluenesulfonyl chloride and 400ml of pyridine was refluxed 20 hours. The mixture was evaporated to dryness. The residue was slurried with a mixture of water and ethyl acetate, then filtered. Recrystallization from ethanol afforded trans-4b, 5, 6, 7, 8, 9-HEXAHYDRO-4b-PHENYL-5-(p-TOLYLSULFONYL)ISOINDOLO[2,1-a]-11-H-BENZIMIDAZOL-11-ONE, mp. 213–5°C.

Anal: Calculated for $C_{27}H_{26}N_2O_3S$: C,70.71; H,5.71; N,6.70. Found C,70.47; H,5.32; N,6.25.

Fifty-three grams of the above material and 120ml of 90% sulfuric acid were heated in a steam bath for 1 hour, then left at room temperature for 19 hours. The mixture was quenched with 1500ml of ice water. The mixture was filtered and the filtrate was made basic with 50% sodium hydroxide solution. The precipitated solid was separated by filtration and washed with water. Two recrystalizations from ethanol-ethylacetate afforded trans 5a, 6, 7, 8, 9, 9a -HEXAHYDRO-11-PHENYL-11 H-ISOINDOLO[2,1-a] BENZIMIDAZOL-11-OL, mp. 176–8°C.

Anal: Calculated for $C_{20}H_{20}N_2O$: C,78.91; H,6.62; N,9.21. Found C,78.65; H,6.52; N,9.11.

EXAMPLE X

By analogous procedures the following compounds are prepared:

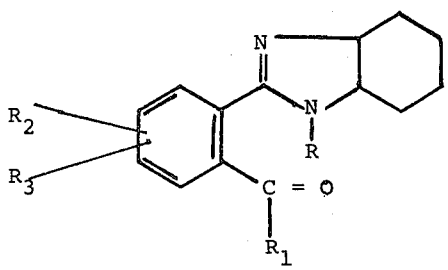

| $R_2$ | $R_3$ | $R_1$ | R |
|---|---|---|---|
| 6-bromo | hydrogen | p-iodophenyl | Methyl |
| 7-methoxy | hydrogen | 3,4-dimethylphenyl | methyl |
| 6-chloro | 7-chloro | p-methoxyphenyl | hydrogen |
| 6-methyl | hydrogen | trifluoromethylphenyl | ethyl |
| 6-methyl | 7-methyl | 2,5-dibromophenyl | hydrogen |
| 5-ethoxy | hydrogen | 3,4-dimethoxyphenyl | methyl |
| 6-methoxy | 7-methoxy | phenyl | n-butyl |
| 8-iodo | hydrogen | p-propoxyphenyl | methyl |
| 6-fluoro | 7-fluoro | phenyl | n-butyl |
| hydrogen | hydrogen | 2,5-dipropoxyphenyl | hydrogen |
| 6-ethyl | hydrogen | p-fluorophenyl | hydrogen |
| 7-propyl | hydrogen | 3,4-diethylphenyl | methyl |
| 6-ethyl | 7-ethyl | phenyl | hydrogen |
| hydrogen | hydrogen | o-chlorophenyl | methyl |
| 7-ethyl | hydrogen | phenyl | methyl |
| hydrogen | hydrogen | 2,5-dibutylphenyl | hydrogen |
| 6-ethoxy | hydrogen | p-chlorophenyl | n-propyl |
| hydrogen | hydrogen | m-chlorophenyl | hydrogen |
| 6-n-propyl | 7-n-propyl | 4-fluorophenyl | hydrogen |
| 6-methyl | hydrogen | 3,4-dichlorophenyl | hydrogen |
| 6-n-butyl | hydrogen | 4-ethoxyphenyl | ethyl |
| 6-bromo | 7-bromo | 4-bromophenyl | n-propyl |
| 6-chloro | hydrogen | phenyl | methyl |

We claim:

1. The pharmaceutically acceptable acid addition salt of a compound having the formula

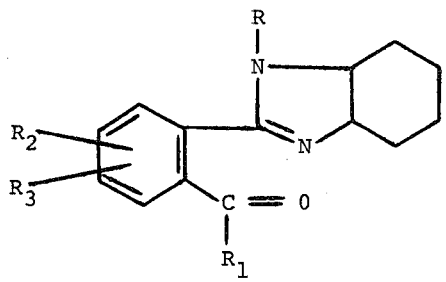

wherein R is hydrogen or lower alkyl, $R_1$ is selected from the group consisting of phenyl, monohalophenyl, dihalophenyl, mono(lower)alkylphenyl, di(lower)alkylphenyl, trifluoromethylphenyl, mono(lower)alkoxyphenyl, di(lower)alkoxyphenyl; $R_2$ is selected from the group consisting of hydrogen, halogen,(lower)alkyl and (lower)alkoxy; $R_3$ is hydrogen when $R_2$ and $R_3$ are dissimilar and when $R_2$ and $R_3$ are the same they are both selected from the group consisting of hydrogen, halogen (lower)alkyl and (lower)alkoxy.

2. The compound of claim 1 which is 4'-chloro--2-(3a, 4, 5, 6, 7, 7a-hexahydrobenzimidazol-2-yl)benzophenone hydrochloride.

3. The compound of claim 1 which is trans 2-(1-ethyl-3a, 4, 5, 6, 7, 7a-hexahydrobenzimidazol-2-yl)benzophenone.

4. The compound of claim 1 which is trans 4'-chloro-2-(1-ethyl-3a, 4, 5, 6, 7, 7a-hexahydrobenzimidazol-2-yl)-benzophenone hydrochloride.

5. The compound of claim 1 which is cis 4'-chloro-2-(1-ethyl-3a, 4, 5, 6, 7, 7a-hexahydrobenzimidazol-2-yl)benzophenone hydrochloride.

6. A compound of the formula:

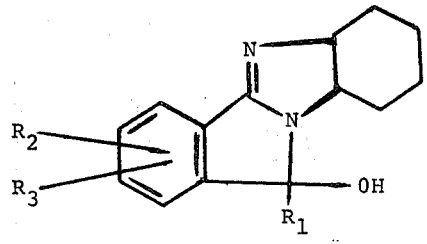

wherein $R_1$ is selected from the group consisting of phenyl, monohalophenyl, dihalophenyl, mono(lower)alkylphenyl, di(lower)alkylphenyl, trifluoromethylphenyl, mono(lower)alkoxyphenyl, di(lower) alkoxyphenyl; $R_2$ is selected from the group consisting of hydrogen, halogen, (lower)alkyl and (lower)alkoxy; $R_3$ is hydrogen when $R_2$ and $R_3$ are dissimilar and when $R_2$ and $R_3$ are the same they are both selected from the group consisting of hydrogen, halogen, (lower)alkyl and (lower)alkoxy.

7. The compound of claim 6 which is trans 5a, 6, 7, 8, 9, 9a,-hexahydro-11-phenyl-11-H-isoindolo[2,1-a]benzimidazol-11-ol.

* * * * *